United States Patent [19]

Burt et al.

[11] 4,020,182

[45] Apr. 26, 1977

[54] PESTICIDAL FORMALDEHYDE CONCENTRATE

[75] Inventors: Leo E. Burt, Robbinsville, N.C.; Stephen E. Frazier, Orlando, Fla.

[73] Assignee: Leo E. Burt, Robbinville, N.C.

[22] Filed: Nov. 21, 1974

[21] Appl. No.: 525,830

Related U.S. Application Data

[63] Continuation-in-part of Ser. No. 349,796, April 10, 1973, abandoned, which is a continuation-in-part of Ser. No. 187,900, Oct. 8, 1971, abandoned.

[52] U.S. Cl. .................................. 424/327; 71/30; 71/113; 424/317; 424/334
[51] Int. Cl.² ..................... A01N 9/20; A01N 9/24; C05C 9/00
[58] Field of Search .......... 424/349, 796, 305, 317, 424/327, 334, 308; 260/501.2; 71/30, 113

[56] References Cited

UNITED STATES PATENTS 2,110,943  3/1958  Remensnyder .......................... 71/3

OTHER PUBLICATIONS

The Merck Index, 8th Ed. – Merck and Co., Inc., p. 540, (1968).
The Merck Index, 8th Ed., Merck and Co., Inc. p. 65 (1968).
U.S. Dispensery–Wood–pp. 117–118, 1936.

Primary Examiner—Albert T. Meyers
Assistant Examiner—D. W. Robinson

[57] ABSTRACT

The composition of matter including an aqueous solution of formaldehyde, a water-soluble hydrazinium salt, and a water-soluble ammonium salt provides a pesticide concentrate that when diluted, is predictably stable; may be used safely in soil or on foliage and around the roots of growing plants; and evidences controlled released properties.

2 Claims, No Drawings

PESTICIDAL FORMALDEHYDE CONCENTRATE

REFERENCE TO RELATED APPLICATIONS

The present application is a continuation-in-part of applicants' copending application Ser. No. 349,796, filed Apr. 10, 1973, now abandoned, which in turn is a continuation-in-part of applicants' copending application Ser. No. 187,900, filed Oct. 8, 1971, now abandoned.

BACKGROUND OF THE INVENTION

Plant and vegetation insect and disease control presently comprehends the use of a wide variety of chemical compositions which may be applied in spray or dust form or both and which are selected on the basis of a particular disease to be controlled in the type of plant infested. Care must be taken to accurately identify the insect, fungus, or other disease producing agent involved and to select the proper pesticide to effectively combat the disease without causing damage to the plant or vegetable as a result of the pesticide.

Soil disease is another source of plant damage, the control of which is based on a program of either plant rotation or soil sterilization or a combination of both. By plant rotation, the susceptible plant or vegetable is replaced by one resistant to the damaging condition. The condition is, in effect, starved away before the susceptible plant or vegetable is replanted in the same location. Where a program or plant rotation cannot be practiced, or is not effective in controlling the condition, then the soil must be sterilized, which is generally accomplished by soil fumigation. A suitable fumigant is worked into the soil to release fumes that are lethal to the disease-causing agent. It is necessary to allow sufficient time to elapse between the soil treatment and planting of seeds or seedlings to permit escape of the fumes which, in most cases, would be harmful to the plants.

Treatments of the type described in the preceding paragraph are used to control disease-causing agents such as fungus, bacteria and the like, as well as nematodes, which are parasitic worms that feed on plants and vegetation. Obviously, however, both the crop rotation and the known soil fumigation methods must be implemented prior to planting and cannot be considered once the seeds or seedlings are in the ground. Therefore, when ground disease exists but is not recognized and treated before planting, the only recourse is to maintain good growing conditions, insofar as possible, in hopes that the harmful condition will not seriously retard growth or reduce yields of the plant and vegetation effected. Plant rotation or soil fumigation can then be practiced before the next planting season.

The gardener or agronomist therefore faces the difficult problem of having to correctly identify the pestilence that is attacking or might attack his growing things. If, in the case of affected plants, the wrong insect or fungus is identified or improper pesticide selected, the price that must be paid is ineffective control of the pestilence or damage to the growing plants. If, however, the condition is nematode infestation or some other undesired soil disease condition that is not diagnosed and properly treated before the crop is planted, the gardener is left substantially helpless with regard to his growing season to implement a treatment.

An agricultural pesticide useful in preventing the growth of a variety of plant infestations which could be applied either to the soil, around the roots of growing plants, or directly onto the foliage of a growing plant, such as grass, would be most useful to the gardener or agronomist and would avoid much of the uncertainty that now exists.

SUMMARY OF THE INVENTION

Accordingly it is an object of this invention to provide a single treatment pesticide effective against certain types of insects, fungus, bacteria and disease-producing organisms that prey on plants and vegetation and the soil therearound.

It is an additional object of this invention to provide a pesticide formulation for the control of fungus; bacteria; nematodes; certain small insects such as mites, flies, scale insects, caterpillar, and aphids; disease and other pestilence that attack growing plants and vegetation, and which has no harmful effects to the plants being treated.

It is yet another object of this invention to provide a pesticide formulation of the type described which is longer lasting and effective over a longer period of time.

It is still another object of this invention to provide a pesticide formulation of the type described which has some attendant fertilizer characteristics.

Other objects of the present invention, if not specifically set forth herein will be obvious to the skilled artisan upon a reading of the detailed description of the invention which follows.

DETAILED DESCRIPTION

Generally, the objects of the present invention are achieved by an agricultural pesticide formulation comprised of an aqueous solution of formaldehyde, a water-soluble hydrazinium salt, and a water-soluble ammonium salt. Preferably, these compounds are present in a concentrated formulation in a ratio of 30–50 parts by weight formaldehyde: 0.5–3.5 parts by weight hydrazinium salt: 0.5–3.5 parts by weight ammonium salt, said concentrated formulation being diluted with water before application.

Such a formulation provides a pesticide formulation in which formaldehyde is the active pesticidal ingredient. Formaldehyde alone is not suitable as a pesticide for several reasons: it is unstable, it is phytotoxic, and has undesirable release properties. Actually the three aforementioned problems are interrelated in the following way. Formalin, the commercially available solution of formaldehyde gas in water used alone as a pesticide, releases free formaldehyde very slowly for a few days, so slowly as to be ineffective as a pesticide. Then the free formaldehyde is released very rapidly, so rapidly as to be phytotoxic to foliage and growing plants.

However, upon combining the formaldehyde or formalin with a hydrazinium salt, and an ammonium salt, a formulation is provided in which the release of free formaldehyde is controlled so as to be effective over long periods of time without the phytotoxic effect that would be realized from the use of formaldehyde alone. The reason for the controlled, non-phytotoxic release is that upon combination with the hydrazinium salt and the ammonium salt, a small amount (approximately 10%) of the formaldehyde is permanently combined with the hydrazinium salt and ammonium salt which will never be released. The remaining major portion of the formaldehyde, however, is available for release in three ways: first, a very small amount (less that 1%) is immediately released as free formaldehyde; the remainder of the available formaldehyde forms polymeric formaldehyde, either of the short chain type (less than 12 carbon atoms long) or the long chain type (more than 12 carbon atoms long). The polymeric formaldehyde is released slowly by one molecule at a time splitting off from the chain and vaporizing. The short chain type releases formaldehyde faster than the long chain type. The result is a steady release of free formaldehyde wherein a uniform amount remains present over the life of the formulation to act as a pesticide.

The relative amounts of formaldehyde, hydrazinium salt, and ammonium salt stated hereinabove are preferred, however not critical unless varied considerably. For example, a test, wherein the formulation comprised a molar ratio of ingredients as follows: formaldehyde: 1,1-dimethylhydrazine oxalate: ammonium benzoate=132:1.3:1, gave very satisfactory results. Where the amount of hydrazine was increased more than five-fold, a marked increase occurs in the percentage of short chain polymers to such an extent that the early rate of release of free formaldehyde rises to such a point that the phytoxic effect occurs. Also the amount of polymeric formaldehyde which will not release is considerably increased making the formulation less effective in the later stages. It should also be noted that additions of hydrazinium salts and ammonium salts considerably below the lower limits of the range would result in an insufficient reaction with the formaldehyde to form polymeric formaldehyde, with the attendant phytotoxicity problem. Therefore the balance of the three ingredients is important, although the specified ranges may be varied to a limited degree.

The particular hydrazinium salt employed does not appear to be critical to the utility of the present invention, so long as the salts are water-soluble. This is explained in that tests have showed that it is the hydrazine that reacts with the formaldehyde, not the oxalate, or chloride. For reasons hereinafter noted, 1,1-dimethylhydrazine oxalate is a preferred hydrazinium salt, although, as explained above, other water-soluble, hydrazinium salts such as hydrazine monohydrochloride, and methylhydrazine sulfate may also be used (See Examples XI through XIV). The water-soluble hydrazinium salts of the organic acids, especially oxalic, citric and tartaric acids, are generally preferred in the present invention.

Also, the particular ammonium salt employed is not critical to the present invention, because it is the ammonium that reacts with the formaldehyde to form polymeric formaldehyde, not the benzoate or citrate parts of the ammonium salt which do not react. Representative ammonium salts include the water-soluble salts of organic acids, such as ammonium benzoate and ammonium citrate. (See Examples XII and XIV.)

While the present formulations may be prepared by adding the aforesaid compounds to water and mixing, or, more practically, adding the hydrazinium and ammonium salts to formalin, the commercial form of formaldehyde comprised of 37-39 percent formaldehyde in water, the formulation is preferably prepared in the form of two concentrated solutions which are subsequently combined and diluted to a degree depending on the particular end use. More specifically, it is preferred to dissolve the hydrazinium salt in formalin to form a first concentrate. The ammonium salt is separately dissolved in water to form a second concentrate. After homogeneous solutions have been obtained, the two concentrates are mixed and diluted.

Of the hydrazinium salts useful in the present invention, 1,1-dimethylhydrazine oxalate, $(CH_3)_2NNH_2H_2C_2O_4$, has been found to be extremely effective as an additive for the formaldehyde, so that the formaldehyde will be more slowly released and effective over longer periods of time. Moreover, the 1,1-dimethylhydrazine oxalate is more readily commercially available, functions secondarily as a fertilizer as well as a slow release additive, and exhibits no possible carcenogenic effects as is the case with some hydrazinium salts. To illustrate the preferred method of preparing the present formulations, 1,1-dimethyhydrazine oxalate is added to an aqueous solution of 37-39% formaldehyde in an amount of 2.3-3.7% by weight to form a first concentrated solution A.

A second concentrated solution B is formed by mixing ammonium benzoate, $NH_4OOCC_6H_5$ in water in an amount from 8.5-10.5% by weight.

The components of solution A are mixed and allowed to stand for 48 hours in a closed container at room temperature. Solution B is then added to solution A in a ratio of 16-20:100 by weight. Solution B containing ammonium benzoate changes the pH of solution A to a more basic or neutral formulation, which prevents burns to plants and soil. Also, as discussed hereinabove, the ammonium benzoate enhances the slow release of the formaldehyde to make the formulation more long lasting.

After solutions A and B are combined, the resulting solution is diluted with water to form a final formulation, varying in concentration depending on the use. For example, for use with tomatoes, vegetables and other truck crops, 1 quart of the final solution is added to 50 gallons of water. Where the formulation is to be used on fruit trees, 3 gallons of the final solution is added to 500 gallons of water.

In the following examples there are described several preferred embodiments to illustrate the invention, however the invention is not intended to be limited to the specific embodiments described.

EXAMPLE I

A first concentrated solution A was formed by adding 1,1-dimethylhydrazine oxalate to an aqueous solution of 37% formaldehyde in an amount of 2.3-3.7% by weight and allowed to stand 48 hours in a closed container at room temperature. A second concentrated solution B was formed by mixing ammonium benzoate in water in an amount of 9.1% by weight. Solution B was then added to solution A in the amount of 16-20 parts by weight of B to 100 parts by weight of A to give a final concentrated mixture M.

EXAMPLE II

A sample of soil was tested and found to contain 17 various types of nematodes including root rot nematodes. A formulation was mixed together using 1 quart of the final concentrated mixture M of Example I added to 50 gallons of water. When the ground was broken and the furrows prepared, the formulation was poured into the bottom of the furrow. The particular amount used is not critical, however it has been found that about 50 gallons of the formulation per acre produces very satisfactory results.

Tomatoes, beans, radishes and cabbages were immediately planted in the furrows and the furrows covered over. After approximately 3 weeks, the soil was again tested, and it was found that the soil was completely free of any nematodes which had been previously present.

EXAMPLE III

A formulation was prepared by adding mixture M to water in a ratio of 1 part of mixture M to 150–200 parts of water and applied by spraying to the foliage of tomatoes, squash, cucumbers, and grapes. Although not critical, it was found that approximately 50 gallons per ¼ acre of the formulation was a satisfactory amount. The formulation was effective in the control of early and late blights of tomatoes, downy mildew and blights of squash and cucumbers, and black rot on grapes. It was also noticed that rose black spot, plant lice and mites were completely controlled on all plants with which the preparation was used.

EXAMPLE IV

A spraying mixture formulation was prepared by adding 3 gallons of the concentrated mixture M of Example I to 500 gallons of water, and was applied to orange, peach, lemon and lime trees for the treatment of snow scale. Treatment of the trees was performed at such time when the trees were free from moisture from dew or precipitation and substantially dry and applied in such quantity as to just wet the trees' foliage. Within one week of the treatment, after only one application, the snow scale condition was eliminated.

EXAMPLE V

A laboratory testing formulation was prepared by diluting concentrated mixture M of Example 1 in the ratios set forth below. The formulation was used against Rhabdolaimus, a saprophyte, obtained from a USDA nematode laboratory in Orlando, Florida and maintained under cultivation. Mortality was determined microscopically.

| Test | Dilution | % Mortality of Nematodes |
| --- | --- | --- |
| 1 | 1 part pesticide soln. 128 parts water | 100 |
| 2 | 1 part pesticide soln. 256 parts water | 100 |
| 3 | 1 part pesticide soln. 500 parts water | 100 |
| 4 | 1:1000 | 100 |
| 5 | 1:2,500 | 100 |
| 6 | 1:5000 | 100 |
| 7 | 1:10,000 | 100 |
| 8 | 1:12,000 | 84 |
| 9 | 1:25,000 | 80 |
| 10 | 1:50,000 | 50 |
| 11 | 1:100,000 | 30 |

EXAMPLE VI

Tomato roots infested with nematodes were dipped for 5 seconds in a diluted pesticide solution formed from the concentrated mixture M of Example I. Using all dilutions from 1:128 to 1:25,000, 100% kill was observed microscopically. At dilutions 1:50,000 and 1:100,000, 60% to 75% kill of nematodes was observed.

EXAMPLE VII

The pesticide solution formed from the concentrated mixture M of Example I was tested on a fungi culture of *Aspergillus niger*, ATCC. Using all dilutions from 1:128 to 1:25,000, the following results were obtained:

| Test | Dilution | Effective Kill Zone, mm |
| --- | --- | --- |
| 1 | 1:128 | 2 |
| 2 | 1:256 | 1.5 |
| 3 | 1:500 | 1.0 |
| 4 | 1:1000 | 0.5 |
| 5 | 1:2,500 | no overgrowth |
| 6 | 1:5,000 | no overgrowth |
| 7 | 1:10,000 | no overgrowth |
| 8 | 1:12,000 | no overgrowth |
| 9 | 1:25,000 | overgrowth observed |

EXAMPLE VIII

A pesticide formulation formed from the concentrated mixture M of Example I using all dilutions from 1:128 to 1:100,000 was tested with a culture of *Staph. aureus* FDA with the following results:

| Test | Dilution | Effective Kill Zone, mm |
| --- | --- | --- |
| 1 | 1:128 | 19 |
| 2 | 1:256 | 15 |
| 3 | 1:500 | 13 |
| 4 | 1:1000 | 10 |
| 5 | 1:2,500 | 8 |
| 6 | 1:5,000 | 6 |
| 7 | 1:10,000 | 4 |
| 8 | 1:12,000 | 2 |
| 9 | 1:25,000 | no overgrowth |
| 10 | 1:50,000 | no overgrowth |
| 11 | 1:100,000 | overgrowth |

EXAMPLE IX

A pesticide formulation formed from the concentrated mixture M of Example I using a dilution of 3:500 was tested on orange leaves and orange branches heavily infested with various insects such as rust mites, aphids, white flies, tea scale, wax scale, lecanium scale, and oyster-shell scale. The infested leaves were dipped in the formulation and allowed to drain off in a 200 ml Pyrex flask for five minutes, then transferred to a petri-dish plate. The following table indicates the percentage of each insect killed after prescribed times:

|  | 6 hrs. | 12 hrs. | 24 hrs. | 36 hrs. | 48 hrs. | 72 hrs. | 120 hrs. |
| --- | --- | --- | --- | --- | --- | --- | --- |
| Rust mite | 10% | 32% | 52% | 81% | 90% | 90% | 92% |
| Aphid | 100% | | | | | | |
| White flies | 82% | 100% | | | | | |
| Tea scale | 9% | 15% | 29% | 53% | 81% | 81% | 83% |
| Wax scale | 7% | 18% | 30% | 48% | 50% | 50% | 50% |

EXAMPLE X

A pesticide formulation formed from the concentrated mixture M of Example I using a dilution of 3:500 was tested on tobacco bud worms (heliothisviresens) and saltmarsh caterpillars. Fresh leaves of lettuce were dipped in the pesticide formulation and allowed to drain. The treated leaves were then placed in a petri-dish plate and the test insect specimens were placed upon leaves in petri-dishes. The following table indicates the percent of insects killed after 6, 12 and 24 hours:

|  | 6 hrs. | 12 hrs. | 24 hrs. | Total Killed | Survived |
|---|---|---|---|---|---|
| Tobacco budworm | 12/100 | 20/100 | 45/100 | 77/100 | 23 |
| Saltmarsh catapillar | 15/100 | 37/100 | 21/100 | 73/100 | 27 |

EXAMPLE XI

Another pesticide formulation was prepared by combining 81.6% of formalin and 3.8% by wt. hydrazine monohydrochloride with 14.5% of a 9% solution of ammonium benzoate in water. The resultant concentrated formulation was diluted in a ratio of 1:96 with water and used as a spray at a rate of 2 gallons per acre on a 10 by 10 foot area of grass severely damaged by brown patch. After 2½ weeks, the brown patch had disappeared and the growth of the grass was completely restored.

EXAMPLE XII

A formulation was prepared in the manner described in Example X except that a 1.8% solution of ammonium citrate was substituted for the ammonium benzoate solution. Equivalent results were observed in the treatment of brown patch.

EXAMPLE XIII

Another formulation was prepared by combining 83.6% formalin and 1.8% by wt. methylhydrazone sulfate with 14.6% of a 9% solution of ammonium benzoate in water. Use of this concentrated formulation in the manner described in Example X also resulted in the elimination of brown patch and restoration of grass growth.

EXAMPLE XIV

A formulation was prepared in the manner of Example XII except that a 1.8% solution of ammonium citrate was substituted for the ammonium benzoate solution. Equivalent results were observed in treating brown patch.

While the use of sprays, capsules, and formulations containing formaldehyde for disinfecting dwellings, ships, storage houses and the like, as a germicide and fungicide for cut plants and vegetables, and for destroying flies and other insects is known, this is believed to be the first formaldehyde solution adapted for effective use directly on growing plants for the control of insects, fungus, and other disease-producing agents. Also, the use of a formaldehyde solution, as described herein, is believed to be the first treatment for plants and vegetation that has been found to be effective against nematodes, fungus and other undesirable soil conditions that can be applied to the soil around a growing plant. The formulation may be applied directly to the foliage and ground surrounding growing plants without detrimental effects to the plant itself.

It will be apparent to the skilled artisan that the foregoing description is intended to be of an illustrative nature and that many modifications and variations thereof can be made without departing from the spirit and scope of the invention.

What is claimed is:

1. A concentrated pesticidal composition for use upon dilution with water on foliage of growing plants, around roots, on grass, and in the surrounding soil, said diluted composition being non-phytotoxic, anti-fungal, anti-bacterial, anti-nematode, and also effective against certain small insects such as mites, flies, scale insects, caterpillars, and aphids, said concentrated composition comprising in aqueous solution 30–50 parts by weight formaldehyde; 0.5–3.5 parts by weight of a hydrazinium salt selected from the group consisting of 1,1-dimethylhydrazine oxalate, hydrazine monohydrochloride, and methylhydrazine sulfate; and 0.5–3.5 parts by weight of an ammonium salt selected from the group consisting of ammonium benzoate and ammonium citrate.

2. A concentrated pesticidal composition for use upon dilution with water on the foliage of growing plants, around roots, on grass, and in the surrounding soil, said diluted composition being non-phytotoxic, anti-fungal, anti-bacterial, anti-nematode, and also effective against certain small insects such as mites, flies, scale insects, caterpillars, and aphids, said composition comprising in aqueous solution 30–50 parts by weight formaldehyde, 0.5–3.5 parts by weight 1,1-dimethylhydrazine oxalate, and 0.5–3.5 parts by weight ammonium benzoate.

* * * * *